United States Patent [19]

von Halasz

[11] 3,962,358

[45] June 8, 1976

[54] PROCESS FOR PREPARING PERFLUORONONANES

[75] Inventor: Sigmar-Peter von Halasz, Kelkheim, Taunus, Germany

[73] Assignee: Hoechst Aktiengesellschaft, Frankfurt am Main, Germany

[22] Filed: June 20, 1974

[21] Appl. No.: 481,460

[30] Foreign Application Priority Data
June 23, 1973 Germany............................ 2332097
Mar. 2, 1974 Germany............................ 2410028

[52] U.S. Cl............................ 260/653; 210/653.9
[51] Int. Cl.² ................... C07C 19/08; C07C 17/04
[58] Field of Search .......................... 260/653.9, 653

[56] References Cited
UNITED STATES PATENTS
2,013,030  9/1935  Calcott et al. .................... 260/653.9
3,149,170  9/1964  Clark et al. ...................... 260/653.9

OTHER PUBLICATIONS

Lovelace et al., Aliphatic Fluorine Compounds, p. 20 (1958).
Hudlicky, Chemistry of Inorganic Fluorine Compounds, p. 68 (1962).
von Halasz et al., Chem. Ber. 106, 2950–2959 (1973).
von Halasz et al., Tetrahedron Letters 24, 2129–2132 (1974).

*Primary Examiner*—D. Horwitz
*Attorney, Agent, or Firm*—Curtis, Morris & Safford

[57] ABSTRACT

By reacting a perfluoro-nonene of the general formula $C_9F_{18}$ in the liquid phase with elementary fluorine a perfluorononane of the general formula $C_9F_{20}$ is formed at high yield.

9 Claims, No Drawings

PROCESS FOR PREPARING PERFLUORONONANES

Perfluoro-alkanes are non-inflammable and resistant to acids, bases, and oxidizing agents and belong to the most stable organic substances known. Due to their thermal and chemical stability and to their dielectric properties they are appropriate for many application fields so that a profitable and simple process for the preparation of substances of this classification is of special interest.

Processes are known, wherein perfluoro-alkanes are prepared by reacting the corresponding saturated or unsaturated hydrocarbons in the vaporous phase with cobalt-trifluoride (E. J. Barber, L. L. Burger and G. H. Cady, J. Am. Chem. Soc. 73, 4241 (1951)). The fluorination of hydrocarbons with elementary fluorine — mostly while diluting it with nitrogen is successful by reaction in the gaseous phase with silver-plated copper catalysts (G. H. Cady, A. V. Grosse, E. J. Barber, L. L. Burger and Z. D. Sheldon, Ind. eng. Chem. 39, 290 (1947)). Most of these processes, however, are plagued by the formation of by-products such as high portions of fragments and of dimeric, trimeric and polymer products (formation of tar). Furthermore, this reaction type yields for each newly formed O — F— bond an equivalent quantity of hydrogen fluoride.

Though the corresponding perfluoro-alkanes are obtained by electro-fluorination of hydrocarbons at more or less good yield rates (H. J. Simons, J. Electrochem. Soc. 95, 47 (1949)), this way of a synthesis requires a considerable expenditure in equipment and energy and partially leads to the fragmentation of the carbon skeleton. It is further known that by reacting perfluorolefines with elementary fluorine moderate yields of the corresponding perfluorinated alkanes can be obtained (W. A. Sheppard and C. M. Sharts, Organic Fluorine Chemistry, 1st edit., pg. 53, Benjamin, New York 1969; E. Forche in "Methoden der organischen Chemie (Houben-Weyl-Muller), 4th edit., vol. V/3, pg. 12, Thieme, Stuttgart 1962; J. M. Tedder in "Advances in Fluorine Chemistry (Stacey-Tatlow-Sharpe), 1st edit., vol. 2, pg. 104, Butterworths, London 1961).

Since the reaction according to the equation

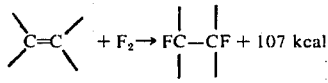

sets free a considerable amount of heat, the formation of fragmentation — products is quite frequent. The addition of fluorine to double bonds of perfluorolefines — as well in liquid as in gaseous phase — proceeds according to a free radical mechanism (A. S. Rodgers, J. Phys. Chem. 69, 254 (1965)), so that the linkage of two C-radicals may yield dimeric products to a large extent (W. T. Miller, Jr., and S. D. Koch, Jr., J. Am. Chem. Soc. 79, 3084 (1957)). In order to keep the formation of these undesirable by-products at a low level, the olefines used were diluted with inert solvents such as $CCl_3F$ or $CF_2Cl-CFCl_2$ and, additionally, the fluorination was performed at low temperatures (down to $-100°C$) and/or with diluted fluorine. But such arrangements affect the reaction speed and the exploitation of the initial materials, especially of fluorine, and they require the work-up to include supplementary steps.

It has further been suggested to use special fluorination-equipment supposed to facilitate keeping the exothermal reaction under control. W. T. Miller suggested to use an equipment consisting of a U-shaped copper vessel (Brit. Pat. No. 839,034 dated June 29, 1960, C. A. 54, 24393e (1960)) for performing the fluorination in the vaporous phase over a liquid surface being constantly renewed by mechanical agitation. Another variety is the equipment for fluorination in the liquid phase such as it has been developed by W. T. Miller, Jr. i.a. (J. Am. Chem. Soc. 86, 51 (1964)). It provides for the use of a high speed metal agitator consisting of a nickel network which finely distributes the gaseous fluorine; the reaction temperature being from $-75°$ to $-120°C$. The operation is performed under fluorine diluted with $N_2$ and/or fluoro-olefine diluted with $CCl_3F$.

Object of the present invention is a process for preparing perfluoro-nonanes having formula $C_9F_{20}$, wherein perfluorononenes of formula $C_9F_{18}$ are reacted in the liquid phase with elementary fluorine at temperatures of from $-40°$ to $+120°C$.

The invention is particularly related to a process for the preparation of perfluoro-nonanes having the formulae

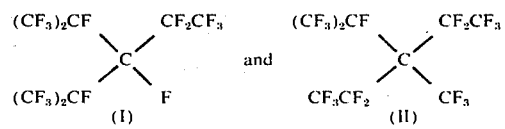

wherein perfluoro-nonenes having the formulae

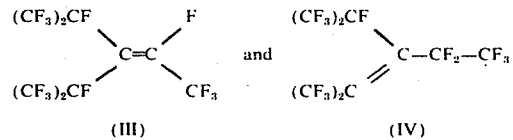

or their mixtures in the liquid phase are reacted with elementary fluorine at temperatures from $-40°$ to $+120°C$.

Further object of the present invention is a process for preparing perfluoro-nonane having the formula

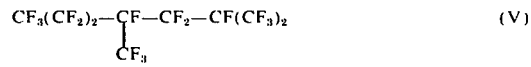

wherein perfluoro-nonenes of the formulae

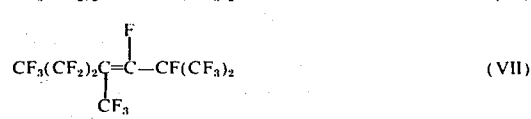

or a mixture of these two cis/trans-isomers in the liquid phase are reacted with elementary fluorine, at temperatures of from $-40°$ to $+120°C$.

The reaction is preferably carried out in absence of inert solvents such as $CCl_3F$ or $CCl_2F_2$, since in that case the purification is simplified. Though their use is possible, it does not contribute any advantage. The dilution of the fluorine with inert gases diminishes the yield. The fluorination is carried out preferably within a temperature range of from 0° to 110°C, the perfluoro-nonane of formula I being preferably prepared at temperatures of from 0° to +80°C, especially from +20° to +70°C, and the perfluoro-nonane of formula II being preferably prepared within a temperature range of from +80° to +120°C, especially of 90° to 110°C. In principle, both perfluorononenes (III and IV) yield upon fluorination the same nonane and it is a matter of the reaction temperature only whether the nonane of formula I or that of formula II prevails.

The reaction as per the invention is generally carried out in the usual way of gas-liquid-reactions, the fluorine being introduced in fine bubbles into the lower tip of a liquid column filled with the nonenes of formulae III and/or IV, after having passed a frit or an equivalent distributing element. This liquid column has advantageously a height surpassing the diameter, at least by three times, preferably by more than five times. The ascending gas bubbles guarantee a sufficiently thorough blending. An additional mechanical agitation is possible, but it does not contribute any advantage.

The height of the liquid column is not of critical importance to the process according to the invention. However, so as to avoid waste gas problems, it is useful to choose such a height, depending on the reaction temperature and the dosage of the fluorine, that at least at the beginning of the reaction all or practically all of the fluorine is reacted. It is an advantage to set up after the reaction vessel another one, similar or identical, being also filled with perfluoro-nonene and wherein the non-reacted fluorine is finally reacted. Therefore, the process of the invention is advantageously run in continuous operation in known manner, for example, by addition of fresh perfluoro-nonene into the upper part of the reactor and by removal of the fluorination-product at the lower tip and subsequent separation of the initial product and the fluorination product.

Neither is a critical factor the dosage of the fluorine, as soon as a regular bubbling up of the fluorine introduced is guaranteed. Fluorine is preferably introduced in its gaseous phase to the same extent as it is reacted, i.e. the higher the layer height of the nonene introduced, the higher may be chosen the inlet rate of the fluorine. Preferably, the process is carried out at normal pressure, though overpressure is also permitted. It is advantageously performed in the absence of light (which emphasizes fragmentation). In case that the reaction is performed under conditions which induce remarkable quantities of fluorine to pass the liquid phase, it is useful to keep the gas volume above the liquid phase as small as possible and/or to cool the gas space on top of the liquid phase. This avoids a gaseous phase reaction which would lead to a fragmentation and a decrease of the yield.

Every reasonably fluorine-resistant material is suitable as material for the reactor and the frit, such as steel, copper, platinum; the reactor may also be lined e.g. with polytetrafluoro-ethylene. In case that the fluorine is sufficiently freed from hydrogen fluoride glass, quartz or ceramics may constitute advantageous materials.

As perfluoro-nonenes are used for the additive reaction according to the equation

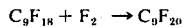

the olefines cited below, in their pure form or as isomeric mixtures:

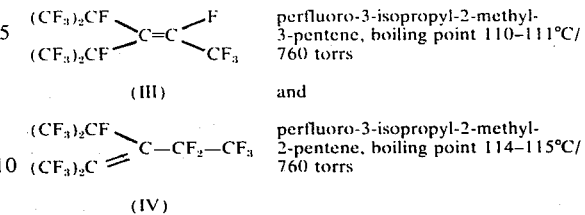

The perfluorononene reactants are obtained easily and with good yields, for example, according to the processes described in German Pat. No. 2,306,439 (1974); S. P. v. Halasz, F. Kluge, Th. Martini, Chemische Berichte, 106, pgs. 2950 – 2959, Sept. 1973; Th. Martini, S. P. v. Halasz, Tetrahedron Letters, No. 24, pgs. 2129 – 2132, June 1974; and W. Brunskill, W. T. Flowers, R. Gregory, Chemical Communications, pgs. 1444 – 1445, 1970.

By addition of fluorine to III or IV, differing only in respect to the position of their double bond, at temperatures preferably from 20° – 70°C about 95 % of the theory of the perfluoro-nonane I having formula

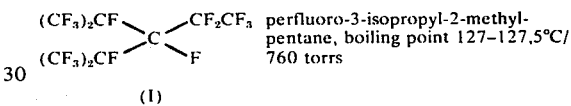

is formed.

Upon reaction of the fluorine with the olefines III and IV in the same manner, but at higher temperatures, preferably from 90° – 120°C, substantial formation occurs - presumably due to the isomerization during the fluorination-step (migration of a trifluoro-methyl-group) - of perfluoro-nonane II having formula

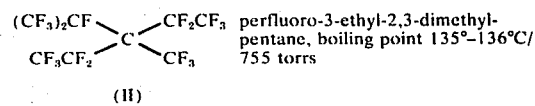

Treating the perfluoro-nonane I with elementary fluorine at 100°C does not result in an isomerization and formation of perfluoro-nonane of structure II. The composition and structures of the compounds I and II are determined by elementary-alalysis as well as by means of their infrared spectrum, mass spectrum and $^{19}F$-NMR-spectrum.

Mixtures of the perfluoro-nonenes VI and VII or of their individual components are obtained in known manner, for example, by treating the a.m. perfluoro-nonenes having formulae

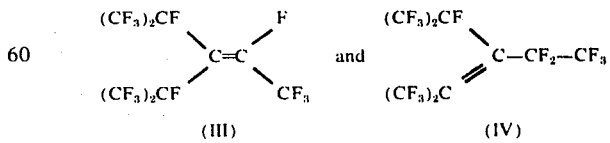

or mixtures of these isomeric perfluoro-nonenes (boiling point 111° – 115°C) in diethylene-glycol-dimethyl ether (diglyme) with cesium fluoride as catalyst, at temperatures of approx. 100°C and by separating eventually the isomers of formulae (VI) and (VII) (boiling point 108°C) by means of fractional distillation or of preparative gas chromatography.

The new perfluoro (2.4-dimethyl-heptane) is formed by addition of fluorine to the perfluoro-nonenes of formulae (VI) and (VII) at temperatures of preferably from +20° to +70°C at a yield rate of up to 96 %, the composition and structure of which is determined by elementary analysis and by means of infrared spectrum, mass spectrum and $^{19}F$ spectrum measuring.

The perfluoro-nonanes I, II and V — easily accessible according to the invention — were unknown in the past. They represent valuable products well appropriate for application in electrical or mechanical systems as hydraulic liquids, dielectrics, turbine fluids, heat transfer media or refrigerating agents due to their thermal and chemical stability and due to their electrical properties. The thus prepared perfluorononanes can also be used as inert solvents or reaction media, especially for reactions with elementary fluorine. Furthermore, the perfluoro-nonanes in question make a suitable active ingredient in blood substitute products, because of their solubility for gases and their surface tensions.

In the past it was considered advantageous to add the fluorine to double bonds in the liquid phase at low temperatures, a method which requires a considerable expenditure in equipment, or to operate with diluents.

In contradiction, it was surprising to find that said perfluoro-nonenes in their liquid phase could be reacted with fluorine to obtain perfluorononanes, also without diluent at normal or higher temperatures with good yields.

The process according to the present invention represents a remarkable technological progress insofar that this low-temperature-procedure and the costs it implies are avoided.

The following examples illustrate the invention:

EXAMPLE 1

The experimental arrangement for elementary fluorination of the olefines III and IV consists of three traps, made of "DURAN" glass (Reg. Trade Mark), being set up one behind the other, dried and rinsed with nitrogen, each of them having a volume of about 300 ml. Into the first trap A — equiped with an interior thermometer and a gas inlet tube reaching down to the bottom of the trap and ending in a glass frit (size G 1) — 450 g (1 mole) of perfluoro-nonene (isomeric proportion from III : IV = 29.7 : 65.9 %) forming a layer height of 20 cm are first introduced at 30°C in the glass frit. Trap A is heated in a water bath.

The next trap B is maintained at −78°C by means of solid $CO_2$, its purpose is the collection of low-boiling cleavage products. The next trap C — alike to trap A equipped with a glass frit and filled with the same perfluoro-nonene — is assigned to the task of absorbing excess fluorine (temperature inside the trap: 30°C) (waste gas purification).

Elementary fluorine is supplied from a commercial steel bottle, measured by means of a previously gauged differential pressure flow meter and introduced into trap A. Before the flow meter and between the traps A and B each an ascending tube manometer is set up for observing the dynamic pressure building up and as a safety valve. The measuring devices are filled in with "VOLTALEF" oil , 10 S (Reg. Trade Mark, Poly-trifluorochloroethylene); the ground joints are sealed with "Voltalef", Graisse 90 (Messrs. Ugine Kuhlmann).

A total of 1.4 mole of fluorine are now introduced at a rate of 0.7 l/h over 45 hours. The interior temperature rises temporarily to 34° – 36°C. The introduction being completed, the weight of the content in trap (A) increased by 26 g; inside trap B 8 g are condensed essentially consisting of low-boiling compounds having formula $C_nF_{2n+2}$, n being smaller than 9.

The gaschromatographic analysis (5.0 m 10 % of hexafluoropropene-expoxide polymers on chromosorb W-AW DMCS 80–100 mesh, 80°C isotherm, 60 ml of He/min.) shows the following composition (surface percentage) of the crude product of the trap A:

| | |
|---|---|
| $C_9F_{20}$ (I) | 94.3 % |
| $C_9F_{18}$ (III) + (IV) | 1.8 % |
| Miscellaneous | 3.8% |

The subsequent fractional distillation over a VIGREUX-column 30 cms long yields a fraction of 444 g (0.91 mole) of compound I at a boiling point of 127° – 127.5°C/760 torrs, corresponding to a 96 % yield, calculated on the perfluorononene used with 96 % purity).

Elementary analysis: $C_9F_{20}$ (I). Calc.: C, 22.15 %; F, 77.85 %; mole-mass 488.1. Found: C, 22.2 %; F, 77.1 %; mole-mass 469 (mass spectr.) $n^{24}$ (Ne 632.8 nm) 1.203.

As it often happens to fluorine compounds, the mole weight found by mass spectrography is diminished by the mass of one (split-off) fluorine atom.

The $^{19}F$-NMR-spectrum of I — registered at 30°C with $CCl_3F$ as internal standard — shows signals at 67.5, 70, 78, 108, 167 and 170 ppm with the relative intensities of 6:6:3:2:2:1. The coupling constants $J_{CF_3}(CF_3CF_2)$—$CF$ (tertiary) are 21.3 Hz.

EXAMPLE 2

The experimental arrangement according to Example (1), slightly modified insofar that the upper part of trap A is water-cooled from the outside and its lower part heated by an oil-bath, is fluorinating at a temperature of 104°C 270 g (0.6 mole) of the mixture of perfluorononene of Example (1).

For this purpose totally 0.84 mole of fluorine are introduced at a rate of 0.9 l/h over 21 hours. The interior temperature in trap A temporarily rises to 106° – 108°C. The introduction being completed, a weight loss of 17.5 g in trap A is noticed; trap B contains 36 g of condensation product, essentially consisting of low-boiling products.

The gaschromatographic analysis (conditions as per Example 1) shows the following composition (area percentage) for the crude product in trap A:

| | |
|---|---|
| $C_9F_{20}$ (II) | 57.3 % |
| $C_9F_{20}$ (I) | 2.5 % |
| $C_9F_{18}$ (III) + (IV) | 8.0 % |
| Miscellaneous | 32.2 % |

Upon fractional distillation over a VIGREUX-column being 30 cm long a fraction of 109.5 g (0.22 mole) of II is obtained at a boiling point of 135° – 136°C/755 torrs, corresponding to a 42 % yield, calculated on perfluorononene reacted (used at 96 % purity).

Elementary analysis: $C_9F_{20}$ (II). Calc.: C, 22.15 %; F, 77.85 %; mole-mass 488.1. Found: C, 21.7 %; F, 78.2

%; mole-mass 469 (mass spectr.) $n^{24}$ (Ne 632.8 nm) 1.201.

The $^{19}$F-NMR-spectrum of II - measuring conditions according to Example (1) -emits the expected signals for the groups a to e showing an intensity proportion of a:b:c:d:e as 3:6:6:4:1 according to the structure

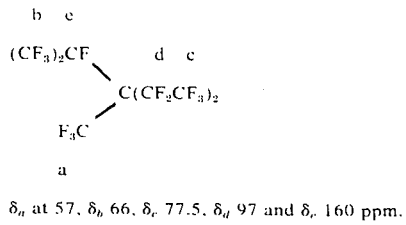

$\delta_a$ at 57, $\delta_b$ 66, $\delta_c$ 77.5, $\delta_d$ 97 and $\delta_e$ 160 ppm.

The signal for the CF-group shows a slight cleavage.

EXAMPLE 3

In the same experimental equipment which had been used for the elementary fluorination of the perfluorononenes III and IV, the isomer mixture of the perfluorononenes VI and VII is reacted with non-diluted fluorine. 90 g (0.2 mole) of $C_9F_{18}$ (isomer proportion VI : VII = 1:3) are introduced at 30°C into the trap equipped with a glass frit. Within 6 hours a total of 0.24 mole of fluorine is fed in, at a rate of 0.9 l/h, the interior temperature climbing to 36° – 38°C. The introduction terminated, the weight of the content in the trap increased by 5 g. In the next trap, cooled with solid $CO_2$, 2 g essentially consisting of low-boiling perfluoroalkanes are condensed.

The gaschromatographic analysis (5.0 m 10 % of hexafluoropropene-epoxide-polymers on chromosorb W-AW DMCS 80–100 mesh, 80°C isothermal) shows a purity of 98.5 % in uniform perfluoro(2,4-dimethylheptane) (V) for the crude product obtained which is purified subsequently by a fractional distillation at normal pressure. It is boiling at 123.5°C/756 mm of Hg.

Elementary analysis: $C_9F_{20}$. Calc.: C, 22.15 %; F, 77.85 %. Found: C, 22.0 %; F, 77.3 %.

The mass spectrum shows the characteristic fragments m/e: 469 (molecular peak - F), 419 (M — $CF_3$), 400 (M —$CF_3$, —F), 381 (M—$CF_3$, —2F) and further fragments.

What is claimed is:

1. A perfluorononane having the formula

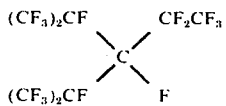

2. A perfluorononane having the formula

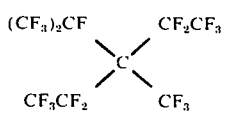

3. A perfluorononane having the formula

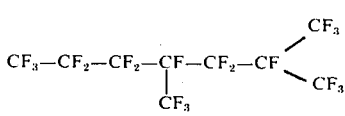

4. A process for preparing a perfluorononane having the formula

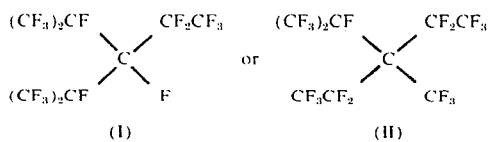

or a mixture thereof which comprises reacting in the liquid phase a perfluorononene having the formula

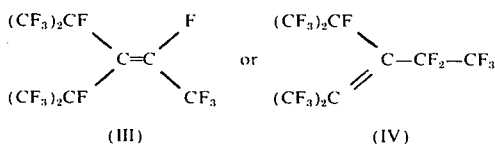

or a mixture thereof with fluorine gas at a temperature from −40° to +120°C.

5. A process for preparing a perfluorononane having the formula

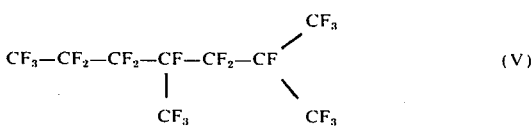

which comprises reacting in the liquid phase a perfluorononene having the formula

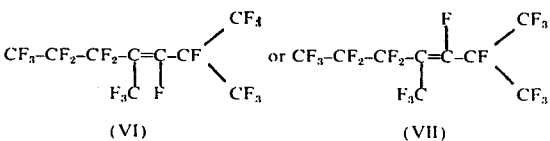

or a mixture thereof with fluorine gas at a temperature from −40° to +120°C.

6. A process according to claim 5, wherein the reaction is carried out at a temperature from +20° to +70°C.

7. The process of claim 4 wherein the reaction is carried out in the absence of diluent.

8. A process for preparing a perfluorononane having the formula

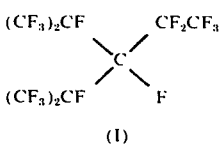

which comprises reacting in the liquid phase a perfluorononene having the formula

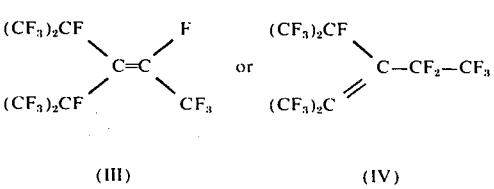

or a mixture thereof with fluorine gas at a temperature from 20°C to 70°C.
9. A process for preparing a perfluorononane having the formula
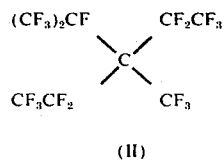
(II)
which comprises reacting in the liquid phase a perfluorononene having the formula
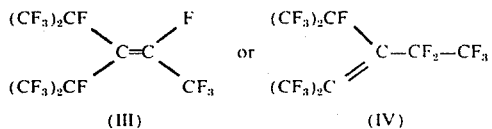
or a mixture thereof with fluorine gas at a temperature of from 90°C to 110°C.
* * * * *